United States Patent [19]

Crossley

[11] 4,304,781

[45] Dec. 8, 1981

[54] TREATMENT OF ULCERS AND HYPERTENSION

[75] Inventor: Roger Crossley, Reading, England

[73] Assignee: John Wyeth & Brother Limited, Maidenhead, England

[21] Appl. No.: 170,366

[22] Filed: Jul. 21, 1980

Related U.S. Application Data

[63] Continuation of Ser. No. 98,420, Nov. 29, 1979, abandoned.

[30] Foreign Application Priority Data

Nov. 30, 1978 [GB] United Kingdom ............... 46722/78

[51] Int. Cl.$^3$ ............................................ A61K 31/44
[52] U.S. Cl. .................................... 424/263; 542/413; 546/270; 546/290; 546/300; 546/301; 546/302; 546/303
[58] Field of Search ........................................ 424/263

[56] References Cited

U.S. PATENT DOCUMENTS 3,235,449  2/1966  Thomas et al. ..................... 546/290

FOREIGN PATENT DOCUMENTS 758658  10/1956  United Kingdom .

OTHER PUBLICATIONS

Yamada et al., J. Org. Chem. vol. 42 (12) 1977, pp. 2180–2182.
Mukaiyama et al., Chem. Letters, (1975) pp. 1159–1162.
Comrie et al., J. Pharm and Pharmacol. 13, (1961), pp. 26–33.

*Primary Examiner*—John M. Ford
*Assistant Examiner*—Bernard Dentz
*Attorney, Agent, or Firm*—George Tarnowski

[57] ABSTRACT

The invention concerns the treatment of ulcers and hypersecretion in a mammal using compounds of the formula I

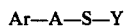

$$Ar-A-S-Y \qquad \qquad I$$

where Ar is phenyl, which may be substituted or cycloalkyl of 5 to 7 carbon atoms, A is saturated or unsaturated lower alkylene which may be substituted by lower alkyl, oxo or hydroxy, S is sulphur and Y is an optionally substituted pyridine, pyridinium, tetrahydropyridine or tetrahydropyridinium radical. Certain novel compounds and pharmaceutical compositions are also disclosed.

11 Claims, No Drawings

TREATMENT OF ULCERS AND HYPERTENSION

This is a continuation of Application Ser. No. 98,420 filed Nov. 29, 1979 and, now abandoned.

The invention relates to a method for treating ulcers or hypersecretion and to heterocyclic compounds useful in pharmaceutical compositions.

During the course of a search for novel anti-ulcer agents we have found that certain compounds containing a pyridine ring substituted by a phenyl alkylthio group, and their quaternary salts, possess anti-ulcer or anti-secretory activity. Some of these compounds are previously known as chemical intermediates or acaricides but most are novel.

Accordingly the invention provides a method for treating ulcers or hypersecretion in a mammal which comprises administering to said mammal an effective amount of a compound of the formula I $$Ar-A-S-Y \qquad I$$

wherein Ar represents a cycloalkyl group of 5 to 7 carbon atoms, or a phenyl group which may be substituted by one or more of the following: halogen, nitro, lower alkoxy, aralkoxy, hydroxy, hydroxyloweralkyl, loweralkoxyloweralkyl, amino, loweralkylamino, diloweralkylamino, loweralkyl, aryl or aralkyl of 7 to 12 carbon atoms or disubstituted by a loweralkylenedioxy radical; A represents a saturated or unsaturated alkylene radical having from 1 to 6 carbon atoms, which may be substituted by lower alkyl of 1 to 6 carbon atoms, oxo or hydroxy, S is sulphur and Y is a radical of formula

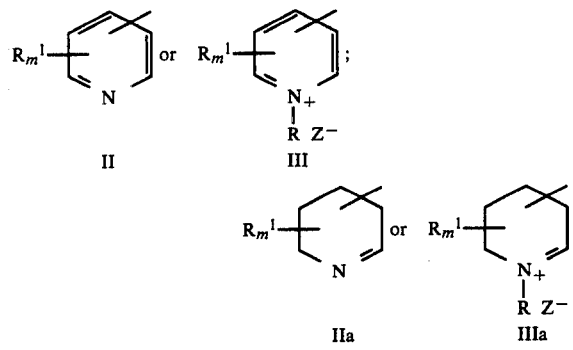

wherein $R^1$ is hydrogen, lower alkyl, hydroxylower alkyl, loweralkoxyloweralkyl, loweralkoxy, halogen, formyl, phenyl, phenylalkyl or acetal alkoxy, halogen, formyl, phenyl, phenylalkyl or acetal $[CH(OR^4)_2$ where $R^4$ is lower alkyl or two $R^4$ radicals are joined to form a lower alkylene chain], R is lower alkyl of 1 to 4 carbon atoms, aryl or aralkyl of 7 to 10 carbon atoms, m is 1 or 2 and $Z^-$ is an anion, or an acid addition salt of a compound containing a radical of formula II, or IIa, with the proviso that when Y is a radical of formula II, Ar is other than aralkoxyphenyl.

The invention also includes pharmaceutical compositions in unit dosage from comprising a compound of formula I as defined above and a pharmaceutically acceptable carrier.

If Ar is a cycloalkyl group it may be cyclopentyl, cyclohexyl or cycloheptyl but cyclohexyl radicals are preferred.

The radical A is preferably a saturated or unsaturated alkylene radical of 1 to 6 carbon atoms which is unsubstituted. A may be methylene, ethylene, propylene, butylene, pentylene or hexylene. Alternatively A may be unsaturated containing at least one double bond, e.g. $-CH=CHCH_2-$. A radicals containing 1 to 4 carbon atoms are preferred.

When R is an aryl or aralkyl group the aryl group or portion may be substituted as described for the phenyl group Ar.

In this specification when a group is substituted by alkyl, this is lower alkyl of 1 to 6 carbon atoms e.g. methyl, ethyl, n-propyl, isopropyl, n-butyl, s-butyl, t-butyl, n-pentyl and n-hexyl. An alkoxy substituent is lower alkoxy in which the alkyl portion is as defined for a lower alkyl group. Whenever the term lower alkyl or lower alkoxy is used as part of another radical e.g. aryl-loweralkyl, the lower alkyl or lower alkoxy portion has 1 to 6 carbon atoms unless otherwise stated.

The anion $Z^-$ is preferably halide, e.g. fluoride, bromide, chloride or iodide or loweralkyl-, aryl- or aralkylsulphonate e.g. methyl sulphonate (mesyl) or p-toluene sulphonate (tosyl).

The acid addition salts of compounds of formula I may be of an organic or inorganic acid e.g. hydrochloric, hydrobromic, phosphoric, sulphuric, nitric, citric, acetic, formic, fumaric, maleic, tartaric, embonic, methane sulphonic and p-toluene sulphonic acids.

For the pharmaceutical carrier any suitable carrier known in the art can be used to prepare the pharmaceutical compositions. In such a composition, the carrier may be a solid, liquid, or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be encapsulating material. In powers the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carriers) is surrounded by carriers, which is thus in association with it. Similarly cachets are included.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 10 to 500 mg or more e.g. 25 mg to 250 mg, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients e.g. aluminium hydroxide, magnesium hydroxide or bismuth carbonate, aluminium glycinate, calcium carbonate, magnesium trisilicate, sodium bicarbonate or the alumina gel described in British specification No. 1,284,394.

Anti-ulcer activity was determined by the stress-induced erosion test of Senay & Levine, Proc. Soc. Exp. Biol. Med., 124, 1221-1223 (1967) and anti-secretory activity by the test of H. Shay, D. Sun and H. Greenstin, Gastroenterology, 1954, 26, 903–913 as exemplified by Beattie et al J. Med. Chem., 20, 714 (1977). Compounds which possess one or both these activities are considered to be anti-ulcer agents which can be used for the treatment of ulcers or hypersecretion in mammals. Nearly all compounds of formula I which we have tested possess one or both of the above activities. However, some compounds show activity in tests for antihypertensive activity.

In another aspect the invention provides as an antiulcer agent a compound of formula I or an acid addition salt thereof as defined above.

Some compounds of formula I are known, for example those in which Ar is unsubstituted phenyl, A is methylene or ethylene, S is sulphur and Y is a radical of formula III wherein R is methyl. These compounds are disclosed in J. Org. Chem. 42, 2180 (1977) as chemical intermediates. Also compounds of formula I in which A is $CH_2$, Y is of formula II wherein $R^1$ is hydrogen and Ar is phenyl or phenyl substituted by alkyl, alkoxy, or one or more halogens or nitro groups are known acaricides, see U.K. patent specification No. 758648. Furthermore compounds of formula I wherein A is —$CH(CH_3)$— or ethylene, Ar is phenyl, Y is a radical of formula II and $R^1$ is hydrogen are disclosed as chemical intermediates in Chemistry Letters, 1975, 1159–1162 (Chem. Soc. Japan). In addition some compounds of formula I wherein Ar is phenyl, A is methylene, Y is of formula III, IIa or IIIa and R is lower alkyl of 1-4 carbon atoms, $R^1$ is hydrogen and Z is halide are disclosed in Ann Chim. 10, 135–177 (1955) see also C.A. 50, 9408–9410 as being of chemical interest.

The invention also includes novel compounds of formula I as defined above and acid addition salts thereof with the provisos that (1) when Ar is phenyl or phenyl substituted by alkyl, alkoxy, or one or more halogen or nitro groups and A is methylene and Y is a radical of formula II, $R^1$ is other than hydrogen, (2) when Ar is phenyl, A is —$CH(CH_3)$— or ethylene and Y is a radical of formula II, $R_1$ is other than hydrogen, (3) when Ar is phenyl, A is methylene, and Y is a radical of formula III, or IIIa, R is other than lower alkyl or $R^1$ is other than hydrogen and (4) when Ar is phenyl, A is ethylene or $COCH_2$ and Y is a radical of formula III, R is other than methyl. Preferably Ar is a substituted phenyl group.

Especially preferred compounds of the invention are those in which Ar is a mono or di-halophenyl radical. The halogen may be fluorine, chlorine, bromine or iodine and may be present in any position in the phenyl ring.

Preferred compounds of the invention are those in which the group Ar—A—S— is at the 2-position of the pyridine or pyridinium ring II or III or tetrahydropyridine IIa or IIIa.

The compounds used in the invention may be prepared by methods known for analogous compounds. The invention includes a method of preparing novel compounds of formula I as defined above wherein provisos (1),(2),(3) and (4) apply which method comprises reacting a compound of formula IV

wherein Ar and A are as defined above and Hal is a halogen atom especially chlorine, bromine, or iodine, with a pyridothione of formula V, pyridothiol of formula VI or piperidine thione of formula VII

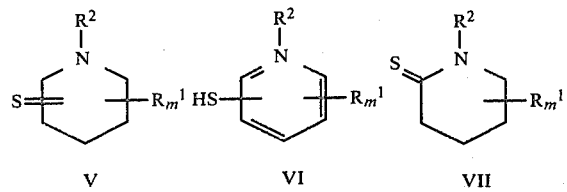

wherein $R^1$ and m are as defined above, $R^2$ is hydrogen, lower alkyl, aryl or aralkyl, and the nitrogen containing ring in formula V contains two double bonds and in formula VI either $R^2$ is absent or if $R^2$ is present the compound of formula VI is in the form of a pyridinium salt.

The invention also includes a method of preparing novel compounds of formula I wherein Y is a radical of formula III or IIIa and R is lower alkyl or aralkyl which comprises reacting a corresponding compound of formula I wherein Y is a radical of formula II or IIa with an alkylating, arylating or aralkylating agent containing the group R and Z, e.g. a lower alkyl or aralkyl halide or lower alkyl-, aryl- or aralkyl sulphonic acid lower alkyl, or aralkyl ester.

A compound I in which $Z^-$ is one particular anion may be converted to another in which $Z^-$ is a different anion by anion exchange, e.g. chloride may be exchanged for iodide by reaction of a chloride of formula I with sodium iodide in ethanol or other suitable solvent.

The amount of compound used in the method of treatment of the invention will depend on the activity of the compound and the needs of the mammal being treated. Doses may range from 1 to 100 mg/kg.

The following examples illustrate the invention:

EXAMPLE 1

2-Benzylthio-1-methylpyridinium bromide

Benzylbromide (1.2 ml) was added to a solution of 1-methyl-2-pyridothione (1.25 g) in acetonitrile (50 ml) and the mixture was heated at reflux for 0.5 hours. The solution was cooled and allowed to crystallise. The crystals were removed by filtration, washed with ether and dried to give the title compound (1.7 g) mp. 190°–192° C. (Found: C, 52.4; 4, 4.8; N, 4.5. $C_{13}H_{14}NSBr$ requires C, 52.7; H, 4.8; N, 4.7%).

EXAMPLE 2

1-Methyl-2-(2-phenylethylthio) pyridinium bromide

A solution of 1-methyl-2-pyridothione (1.25 g) in ethanol (15 ml) was treated with phenylethyl bromide (1.85 g) and the mixture was heated on a steam bath for 4 hours. The residue, after evaporation, was recrystallised twice from propan-2-ol to give the title compound (2.0 g) mp 162°–615° C. (Found: C, 54.3; H, 5.3; N, 4.4. $C_{14}H_{16}NSBr$ requires C, 54.2; H, 5.2; N, 4.5%).

EXAMPLE 3

2-(4-Chlorobenzylthio)-1-methylpyridinium chloride

A solution of 1-methyl-2-pyridothione (1.25 g) and 4-chlorobenzylchloride (1.61 g) in ethanol (10 ml) was heated under reflux for 4 hours. Ether (40 ml) was added whilst hot, the mixture was scratched to induce crystallisation and another 15 ml of ether was added. The product was removed by filtration and dried to give the title compound (2.0 g) mp. 167°–168° C. (Found: C, 54.15; H, 4.75; N, 5.1. $C_{13}H_{13}Cl_2NS$ requires C, 54.55; H, 4.6; N, 4.9%).

EXAMPLE 4

2-(3,4-Dichlorobenzylthio)-1-methylpyridinium chloride

A solution of 3,4-dichlorobenzyl chloride (1.95 g) and 1-methyl-2-pyridothione (1.25 g) in ethanol (10 ml) was heated under reflux for 5 hours. Ether (90 ml) was added and the product was allowed to crystallise. Recrystallisation from propan-2-ol/ether gave the title compound (2.3 g) mp 180°–182° C. (Found: C, 48.9; H, 4.1; N, 4.2. $C_{13}H_{12}Cl_3NS$ requires C, 48.7; H, 3.8; N, 4.4%).

EXAMPLE 5

2-(2,6-Dichlorobenzylthio)-1-methylpyridinium chloride

A solution of 2,6-dichlorobenzyl chloride (1.95 g) and 1-methyl-2-pyridothione (1.25 g) in ethanol (10 ml) was heated at reflux for 4 hours cooled and filtered to give the title compound (2.5 g) m.p. 214°–216° C. (Found: C, 49.1; H, 4.0; N, 4.15. $C_{13}H_{12}Cl_3NS$ requires C, 48.7; H, 3.8; N, 4.4%).

EXAMPLE 6

1-Methyl-2-(4-nitrobenzylthio)pyridinium bromide

A solution of 1-methyl-2-pyridothione (1.25 g) and 4-nitrobenzyl bromide (2.2 g) in ethanol (10 ml) was heated at reflux for 4 hours. After cooling, the product was removed by filtration and recrystallised from ethanol to give the title compound (2.5 g) mp 187°–189°. (Found: C, 46.0; H, 4.0; N, 8.1. $C_{13}H_{13}BrN_2O_2S$ requires C, 45.8; H, 3.8; N, 8.2%).

EXAMPLE 7

1-Methyl-2-(3-phenylpropylthio)pyridinium bromide

3-Phenylpropyl bromide (1.9 g) was added to a solution of 1-methyl-2-pyridothione (1.25 g) in ethanol (10 ml) and the mixture was heated at reflux for 4 hours. The solvent was removed by evaporation and the residue triturated with ether to give a solid which was washed with ether by decantation until the washings were colourless. The solid was removed by filtration and dried to give the title compound as the hemihydrate (2.6 g) mp 85°–90° C. (Found: C, 54.3; H, 5.8; N, 4.2. $C_{15}H_{18}BrNS, \frac{1}{2}H_2O$ requires C, 54.1; H, 5.75; N, 4.2%).

EXAMPLE 8

1-Methyl-2-(3,4-dimethylbenzylthio)pyridinium chloride

A solution of 1-methyl-2-pyridothione (1.25 g) and 3,4-dimethylbenzyl chloride (1.54 g) in ethanol (10 ml) were heated at reflux for 4 hours. Ether (30 ml) was added and the mixture allowed to crystallise. The product was removed by filtration to give the title compound (1.6 g) mp 170° C. decomp. (Found: c, 64.5; H, 6.7; N, 5.0. $C_{15}H_{18}ClNS$ requires C, 64.4; H, 6.5; N, 5.0%).

EXAMPLE 9

1-Methyl-2-(2-phenylpropylthio)pyridinium bromide

A solution of 2-phenylpropyl bromide (1.99 g) and 1-methyl-2-pyridothione (1.25 g) in ethanol (10 ml) was heated at reflux for 4 hours. The solvent was removed by evaporation and the residue was triturated with ether (10×20 ml) for 5 hours. The resulting solid was removed by filtration to give the title compound as the hemihydrate (1.4 g) mp 110°–115° C. (Found: C, 53.8; H, 5.6; N, 4.0. $C_{15}H_{18}BrNS \frac{1}{2}H_2O$ requies C, 53.95; H, 5.7; N, 4.2%).

EXAMPLE 10

1-Methyl-2(4-methylbenzylthio)pyridinium bromide

A solution of 1-methyl-2-pyridothione (1.25 g) and 4-methylbenzyl bromide (1.85 g) in ethanol (10 ml) was heated at reflux for 4 hours. Ether (20 ml) was added and the mixture allowed to crystallise. The product was removed by filtration to give the title compound (2.5 g). mp 170° C. decomp. (Found: C, 54.2; H, 5.4; N, 4.4. $C_{14}H_{16}BrNS$ requires C, 54.2; H, 5.2; N, 4.5%).

EXAMPLE 11

1-Methyl-2-(3-chlorobenzylthio(pyridinium chloride

A solution of 1-methyl-2-pyridothione (1.25 g) in ethanol (10 ml) was treated with 3-chlorobenzyl chloride (1.6 g) and the mixture was heated under reflux for 4 hours. Ether (30 ml) was added and the resulting crystals were removed by filtration and dried to give the title compound (2.1 g) mp 182°–184° C. (Found: C, 54.5; H, 4.8; N, 4.7. $C_{13}H_{13}Cl_2NS$ requires C, 54.55; H, 4.6; N, 4.9%).

EXAMPLE 12

2-(Cyclohexylmethylthio)-1-methylpyridinium bromide

A solution of bromomethyl cyclohexane (1.77 g) in hot ethanol (5 ml) was treated with a solution of 1-methyl-2-pyridothione in hot ethanol (5 ml). The mixture was heated under reflux for 4.5 hours and then allowed to cool to room temperature. Diethyl ether was then added and the resulting solid was removed by filtration and dried to give the title compound as the quarter hydrate (1.1 g, 36%) mp. 149°–150.5° C. Found: C, 50.9; H, 6.8; N, 4.3%. $C_{13}H_{20}BrNS \cdot \frac{1}{4}H_2O$ requires: C, 50.9; H, 6.7; N, 4.6%).

EXAMPLE 13

2-(4-Bromobenzylthio)-1-methylpyridinium bromide

A solution of 1-methyl-2-pyridothione (1.25 g) and 4-bromobenzyl bromide (2.3 g) in ethanol (10 ml) was heated at reflux for 4 hours. Ether (10 ml) was added and the mixture was allowed to crystallise. The resulting crystals were removed by filtration and dried to give the title compound (3.0 g) mp 186°–188° C. (Found: C, 41.9; H, 3.7; N, 3.5. $C_{13}H_{13}Br_2NS$ requires C, 41.6; H, 3.5; N, 3.7%).

EXAMPLE 14

2-(((4-Benzyloxy)benzyl)thio)-1-methylpyridinium chloride

4-Benzyloxybenzyl chloride (3.6 g) was dissolved in hot ethanol (10 ml) and 1-methyl-2-pyridothione (1.25 g) was added. The mixture was heated at reflux for 4 hours and cooled. The resultant crystals were removed by filtraion, washed with ether and dried to give the title compound as the monohydrate (3.8 g) mp 196°–198° C. (Found: C, 63.5; H, 6.1; N, 3.6. $C_{20}H_{20}ClNOS$, $H_2O$ requires C, 63.9; H, 5.9; N, 3.7%).

EXAMPLE 15

1-Methyl-2-phenacylthiopyridinium bromide

A mixture of phenacyl bromide (1.99 g) and 1-methyl-2-pyridothione (1.25 g) in ethanol (20 ml) was heated at reflux for 1 hour. The solution was filtered and allowed to crystallise and the resulting crystals were removed by filtration and dried to give the title compound (2.1 g) mp 185°–187° C. decomp. (Found: C, 51.5; 4.4; N, 4.0. $C_{14}H_{14}BrNOS$ requires C, 51.8; H, 4.35; N, 4.3%).

EXAMPLE 16

2-Cinnamylthio-1-methylpyridinium bromide

A solution of cinnamyl bromide (1.75 g) and 1-methyl-2-pyridothione (1.25 g) in ethanol (10 ml) were heated at reflux for 4 hours and cooled. Ether (20 ml) was added and the product which crystallised was removed by filtration, washed with ether and dried to give the title compound as the hemihydrate (1.8 g) mp. 133°–135° C. (Found: C, 54.8; H, 5.2; N, 4.3. $C_{15}H_{16}BrNS$ $\frac{1}{2}H_2O$ requires C, 54.4: H, 5.2; N, 4.2%).

EXAMPLE 17

2-(3-Bromobenzylthio)-1-methylpyridinium bromide

A solution of 3-bromobenzyl bromide (2.3 g) and 1-methyl-2-pyridothione (1.25 g) in ethanol (10 ml) were heated at reflux for 1 hour. Crystals which precipitated on cooling were removed by filtration, washed with ethanol and ether and dried to give the title compound (3.0 g) mp. 190°–192° C. Found: C, 41.3; H, 3.6; N, 3.9. $C_{13}H_{13}Br_2NS$ requires C, 41.6; H, 3.5; N, 3.7%.

EXAMPLE 18

2-((-4-Isopropylbenzyl)thio)-1-methylpyridinium chloride

A mixture of 4-isopropylbenzyl chloride (1.68 g) and 1-methyl-2-pyridothione (1.25 g) in ethanol (10 ml) were heated at reflux for 10 hours. The solvent was removed by evaporation and the residue triturated with ether to give a solid. Recrystallisation from propan-2-ol/ether gave the title compound (1.6 g) mp 154°–157° C. (Found: C, 65.4; H, 7.0; N, 4.7. $C_{16}H_{20}ClNS$ requires C, 65.4; H, 6.9; N, 4.8%.

EXAMPLE 19

2-Benzylthio-3-(diethoxy)methyl-1-phenylpyridinium chloride

A mixture of benzyl chloride (0.6 ml) and 3-formyl-1-phenyl-2-pyridothone (1.05 g) in ethanol (10 ml) was heated at reflux for 4 hours. $Et_2O$ (200 ml) was added and the resulting crystals were removed by filtration and dried to give the title compound as the monohydrate (0.8 g) mp 133°–135° C. (Found: C, 63.9; H, 6.5; N, 3.4 Calc for $C_{23}H_{26}ClNO_3S$ requires C, 63.65: H, 6.5: N, 3.2%).

EXAMPLE 20

2-((2-Fluorobenzyl)thio)-1-methyloyridinium chloride

A mixture of 2-fluorobenzyl chloride (1.5 g) and 1-mehyl-2-pyridothione (1.25 g) in ethanol (10 ml) was heated at reflux for 4 hours. Ether (40 ml) was added and the resulting crystals were removed by filtration, washed with ether and dried to give the title compound (2.4 g) mp 175°–177° C. (Found: C, 57.6; H, 5.15; N, 5.1. $C_{13}H_{13}ClFNS$ requires C, 57.9; H, 4.9; N, 5.2%.

EXAMPLE 21

2((4-Fluorobenzyl)thio)-1-methylpyridinium chloride

A mixture of 4-fluorobenzyl chloride (1.5 g) and 1-methyl-2-pyridothione (1.25 g) in ethanol (10 ml) was heated at reflux for 4 hours. Ether (20 ml) was added and the resultant crystals were removed by filtration and dried to give the title compound (2.4 g) mp 177°–179° C. (Found: C, 57.6; H, 5.1; N, 5.0. $C_{13}H_{13}ClFNS$ requires C, 57.9; H, 4.9; N, 5.2%).

EXAMPLE 22

2-((-3-Fluorobenzyl)thio)-1-methylpyridinium chloride

A solution of 3-fluorobenzyl chloride (1.5 g) and 1-methyl-2-pyridothione (1.25 g) in ethanol (10 ml) was heated at reflux for 4 hours. The solvent was removed by evaporation and the residue was triturated with ether to give a hygroscopic solid which was removed by filtration and dried to give the title compound as the hemihydrate (2.3 g) mp 80°–85° C. (Found, 56.0; H, 4.9; N, 4.6. $C_{13}H_{13}ClFNS$. $\frac{1}{2}H_2O$ requires C, 56.0; H, 4.1; N, 5.0%).

EXAMPLE 23

4-Benzylthio-1-methylpyridinium bromide

A solution of benzyl bromide (1.7 g) and 1-methyl-4-pyridothione (1.25 g) in ethanol (10 ml) were heated at reflux for 2 hours and allowed to cool. The crystals which formed were removed by filtration and dried to give the title compound (1.7 g) mp. 195.8° C. (Found: C, 52.7; H, 4.9; N, 4.5. $C_{13}H_{14}BrNS$ requires C, 52.7; H, 4.8; N, 4.7%). A further 0.8 g was obtained by adding ether (40 ml) to the mother liquors.

EXAMPLE 24

4-((3-Chlorobenzyl)thio)-1-methylpyridinium chloride

A mixture of 3-chlorobenzyl chloride (1.6 g) and 1-methyl-4-pyridothione (1.25 g) in ethanol (10 ml) was heated at reflux for 4 hours. Ether (40 ml) was added and the precipitated crystals were removed by filtrartion and washed with ether and dried. Recrystallisation from ethanol-ether gave the title compound as the quarter hydrate. (1.8 g) mp 170°–171° C. (Found: C, 53.8; H, 4.7; N, 4.65. $C_{13}H_{13}Cl_2NS.\theta H_2O$ requires C, 53.7; H, 4.7; N, 4.8%).

EXAMPLE 25

1-Methyl-2-((3-methylbenzyl)thio)pyridinium chloride

A mixture of 3-methylbenzyl chloride (1.4 g) and 1-methyl-2-pyridothione (1.25 g) in ethanol (10 ml) was heated at reflux for 4 hours. $Et_2O$ (25 ml) was added and the solution was filtered and allowed to crystallise. The crystals were removed by filtration and dried to give the title compound (1.3 g) mp. 185°–187° C. (Found: C, 63.0; H, 6.1; N, 5.1. $C_{14}H_{16}ClNS$ requires C, 63.3; H, 6.1; N, 5.3%)

EXAMPLE 26

2-((4-Methoxybenzyl)thio)-1-methylpyridinium chloride

A mixture of 4-methoxybenzyl chloride (1.4 g) and 1-methyl-2-pyridothione (1.25 g) in ethanol (10 ml) was heated at reflux for 4 hours. Ether (20 ml) was added and the solution was filtered. The crystals which precipitated were removed by filtration and dried to give the title compound as the monohydrate (1.6 g) mp 114°–117° C. (Found: C, 56.45; H, 6.0; N, 4.5. $C_{14}H_{16}ClNOS.H_2O$ requires C, 56.1; H, 6.05; N, 4.7%).

EXAMPLE 27

2-((2-Chlorobenzyl)thio)-1-methylpyridinium chloride

A mixture of 2-chlorobenzyl chloride (1.6 g) and 1-methyl-2-pyridothione (1.25 g) in ethanol (10 ml) was heated at reflux for 4 hours. Ether (40 ml) was added and the solution was filtered. The product which crystallised was removed by filtration and dried to give the title compound as the monohydrate (2.1 g) mp 112° C. solidifies and remelts 164–165° C. (Found: C, 51.51 H, 5.0; N, 4.3. $C_{13}H_{13}Cl_2NS.H_2O$ requires C, 51.3; H, 5.0; N, 4.6%.

EXAMPLE 28

2-(3,5-Dichlorobenzyl)thio)-1-methylpyridinium chloride

A mixture of 3,5-dichlorobenzyl chloride (1.95 g) and 1-methyl-2-pyridothione (1.25 g) in ethanol (10 ml) was heated at reflux for 4 hours. Ether (40 ml) was added and the resulting crystals were removed by filtration and triturated with ether and dried to give the title compound (2.2 g) mp 185°–187° C. (Found: C, 48.7; H, 3.85; N, 4.1. $C_{13}H_{12}Cl_3NS$ requires C, 48.7; H, 3.8; N, 4.4%).

EXAMPLE 29

2-Benzylthio-3-formyl-1-methylpyridinium bromide

A solution of benzyl bromide (0.5 g) and 3-formyl-1-methyl-2-pyridothione (0.44 g) in acetonitrile (10 ml) was heated at reflux for 2 hours. On cooling crystals precipitated which were removed by filtration and dried to give the title compound (0.5 g) mp 168°–170° C. (Found: C, 51.7; H, 4.4; N, 4.3. $C_{14}H_{14}BrNOS$ requires C, 51.9; H, 4.35; N, 4.3%).

EXAMPLE 30

2-Benzylthio-3-hydroxymethyl-1-phenylpyridinium bromide

A solution of benzyl bromide (0.56 g) and 3-hydroxymethyl-1-phenyl-2-pyridothione (0.71 g) in acetonitrile (10 ml) was heated at reflux for 4 hours. On cooling crystals precipitated which were removed by filtration and dried to give the title compound (1.0 g) mp 183°–184° C. (Found: C, 58.8; H, 4.7; N, 3.75. $C_{19}H_{18}BrNOS$ requires C, 58.8; H, 4.7; N, 3.6%.

EXAMPLE 31

4((3-Chloro)benzylthio)pyridine

3-Chlorobenzyl chloride (1.61 g) and 4-mercaptopyridine (1.11 g) in ethanol (10 ml) were heated at reflux for 4 hours and cooled. Crystals which precipitated were removed by filtration and dried to give the title compound as the hydrochloride (1.3 g) mp 222°–224° C. (Found: C, 52.6; H, 4.3; N, 5.1. $C_{12}H_{10}ClNS$ requires C, 52.95; H, 4.1; N, 5.1%).

EXAMPLE 32

1-Methyl-2-((3-nitro)benzylthio)pyridinium chloride

3-Nitrobenzyl chloride (1.71 g) and 1-methyl-2-pyridothione (1.25 g) in ethanol (10 ml) were heated at reflux for 4 hours. Ether (10 ml) was added and the solution was cooled. The resulting crystals were removed by filtration and dried to give the title compound as the monohydrate (2.2 g) mp. 173°–178° C. decomp (softens at 140° C.) Found: C, 49.65; H, 5.0; N, 8.7. $C_{13}H_{13}ClN_2O_2S.H_2O$ requires C, 49.6; H, 4.8; N, 8.9%.

EXAMPLE 33

1-Methyl-2-((2-methyl)benzylthio)pyridinium bromide

A solution of α-bromo-o-oxylene (1.85 g) and 1-methyl-2-pyridothione (1.25 g) in ethanol (10 ml) was heated at reflux for 2 hours. The product which crystallised on cooling was removed by filtration, washed with ether and dried to give the title compound (2.5 g) mp. 210°–214° C. decomp. (Found: C, 54.0; H, 5.2; N, 4.25. $C_{14}H_{16}BrNS$ requires C, 54.2; H, 5.2; N, 4.5%).

EXAMPLE 34

4-Benzylmercaptopyridine

A solution of benzyl bromide (1.71 g) and 4-mercapto-pyridine (1.11 g) in ethanol (10 ml) were heated at reflux for 4 hours. Ether (5 ml) was added and the solution allowed to crystallise. Recrystallisation from ethanol-ether gave the title compound hydrobromide as a quarter hydrate (1.0 g) mp. 202°–204° C. (Found: C, 50.5; H, 4.1; N, 5.3. $C_{12}H_{11}NS,HBr \frac{1}{4}H_2O$ requires C, 50.3; H, 4.3; N, 4.9).

EXAMPLE 35

2-((3-Iodobenzyl)thio)-1-methylpyridinium chloride

A solution of 3-iodobenzyl chloride (2.5 g) and 1-methyl-2-pyridothione (1.25 g) in ethanol (10 ml) was heated at reflux for 6 hours. The solvent was removed by evaporation and the residue was triburated with ether and then with acetone to give a solid which was removed by filtration and dried to give the title compound as a hemihydrate(2.3 g) mp. 192°–194° C.

(Found: C, 40.8; H, 3.75; N, 3.6. $C_{13}H_{13}ClINS$. $\frac{1}{2}H_2O$ requires C, 40.4; H, 3.65; N, 3.6%).

EXAMPLE 36

2-((3-Methoxybenzyl)thio)-1-methylpryridinum chloride

A solution of 3-methoxybenzyl chloride (1.4 g) and 1-methyl-2-pryidothione (1.25 g) in ethanol (10 ml) was heated at reflux for 6 hours. The solvent was removed by evaporation and the residue was triturated with ether and then with acetone to give a solid. This was removed by filtration, washed with acetone and dried to give the title compound as a hemihydrate (1.5 g). mp. 172°–174° C. (Found: C, 57.4; H, 6.2; N, 4.6. $C_{14}H_{16}ClNOS$. $\frac{1}{2}H_2O$ requires C, 57.8; H, 5.9; N, 4.8%.)

EXAMPLE 37

1-Methyl-2-((3-trifluoromethylbenzyl)thio)pyridinium chloride

A solution of 3-trifluoromethylbenzyl chloride (1.95 g) and 1-methyl-2-pyridothione (1.25 g) in ethanol (10 ml) was heated at reflux for 2 hours and allowed to stand at ambient temperature for 16 hours. The solvent was removed by evaporated and the residue was triturated with ether. The resultant crystals were removed by filtration, washed with ether and dried to give the title compound as a hemihydrate (2.3 g) mp 140°–143° C. (Found: C, 51.4; H, 4.3; N, 4.4. $C_{14}H_{13}ClF_3NS$, $\frac{1}{2}H_2O$ requires C, 51.15; H, 4.1; N, 4.3%).

EXAMPLE 38

2-((Benzyl)thio)pyridine

A solution of 2-mercaptopyridine (3.33 g) in warm ethanol (100 ml) was treated with benzyl bromide (3.59 ml). The mixture was heated under reflux for 2.5 hours and then allowed to cool to room temperature. Diethyl ether was added to precipitate the product which was removed by filtration and dried to give the title compound as the hydrobromide (7 g; 83%). mp. 156°–157.5° C. (Found: 51.3; H, 4.55; N, 5.1% $C_{12}H_{11}NS.HBr$ requires: C, 51.1; H, 4.3; N, 5.0%).

EXAMPLE 39

2-((Diphenylmethyl)thio)-1-methyloyridinium bromide

A mixture of 1-methyl-2-pyridothione (1.24 g) and benzhydryl bromide (2.47 g) in ethanol (10 ml) were heated at reflux for 8 hours. The solvent was removed by evaporation and the residue was triturated with ether and with acetone to give a solid which was removed by filtration and dried to give the title compound as a quarter hydrate (1.4 g) mp. 174°–176° C. (Found: C, 60.6; H, 4.95; N, 3.7 $C_{19}H_{18}BrNS,\frac{1}{4}H_2O$ requires C,60.7; H, 4.85; N, 3.7%).

EXAMPLE 40

1-Methyl-2-((4-phenylbutyl)thio)pyridinium bromide

A solution of 4-phenylbutyl bromide (2.13 g) in ethanol (20 ml) was treated with 1-methyl-2-pyridothione (1.25 g) and the mixture was heated under reflux for $5\frac{1}{2}$ hours. It was then allowed to cool to room temperature and diluted with diethyl ether. The resulting solid was removed by filtration and recrystallised from isopropyl alcohol/di-isopropyl ether to give the title compound as a quarter hydrate (1.7 g; 50%) mp. 118°–123° C. (Found: C, 56.4; H, 6.1; N, 3.9% $C_{16}H_{20}BrNS$ requires: C, 56.8; H, 6.0; N, 4.1%.

EXAMPLE 41

1-(4-Nitrobenzyl)-2-(benzylthio)-pyridinium bromide

A mixture of 4-nitrobenzyl bromide (1.08 g) and 2-(benzylthio)pyridine (1.05 g) were heated at 100° C. for 4 hours and cooled. Crystals which formed on trituration with acetone were removed by filtration and dried to give the title compound as a quarter hydrate (1.6 g) mp 160°–162° C. (Found C, 53.8; H, 4.5; N, 6.4%. $C_{19}H_{17}BrN_2O_2S\frac{1}{4}H_2O$ requires C, 54.1; H, 4.2; N, 6.6%).

EXAMPLE 42

2-((4-Benzyloxy)benzylthio)pyridine

A solution of 2-pyridothione (1.1 g) and 4-benzyloxybenzyl chloride (2.5 g) in ethanol was heated at reflux for 4 hours. Crystals which formed on cooling were removed by filtration, washed with ether and dried to give the title compound as the hydrochloride (2.8 g) mp 125°–127° C. (Found: C,64.1; H, 5.8; N, 3.7, $C_{19}H_{17}NOS$. $HCl\frac{3}{4}H_2O$ requires C, 63.9; H, 5.9; N 3.9%). The product is an intermediate for the product of Example 14.

EXAMPLE 43

2-Benzylthio-3,4,5,6-tetrahydropyridine 2-piperidothione (1.15 g) was dissolved in acetone (10 ml) and treated with benzyl bromide (1.7 g). After 3 hours at ambient temperature the resulting solid was removed by filtration, washed with acetone and dried to give the title compound as the hydrobromide (2.3 g) mp 175°–176° C. (Found C, 50.5; H, 5.8; N, 4.9%. $C_{12}H_{15}NS.HBr$ requires, C, 50.35; H, 5.6; N, 4.9%).

EXAMPLE 44

2-Benzylthio-3,4,5,6-tetrahydro-1-methylpyridinium bromide

1-Methyl-2-piperidothione (1.29 g) was dissolved in acetone (10 ml) and treated with benzyl bromide (1.7 g). After allowing the mixture to stand for 3 hours at room temperature a solid formed and was formed and was filtered off, washed with acetone, and dried to give the title compound (1.9 g) mp 163°–167° C. (Found: C, 52.5; H, 6.3; N, 4.8. $C_{13}H_{18}BrNS$ requires C, 52.0; H, 6.0; N, 4.7%).

EXAMPLE 45

1-Benzyl-2-(benzylthio)pyridinium bromide

A mixture of 2-(benzylthio)pyridine (2.01 g) and benzyl bromide (1.71 g) was kept at ambient temperature for 4 days. Trituration at length with ether gave a solid which was removed by filtration and dried to give the title compound (2.2 g) mp 125°–127° C. (Found: C, 61.6; H, 5.2; N, 3.6%. $C_{19}H_{18}BrNS$ requires C, 61.3; H, 4.9; N, 3.8%).

| | Pharmacological Test Results | | | |
|---|---|---|---|---|
| | Stress-induced erosion (Senay & Levine) | | Anti-secretory (Shay et al) | |
| Compound [Product of Example No.] | Dose mg/kg | % inhibition | Dose mg/kg | % change in Vol. |
| 1 | 100 | 75 | 30 | −71 |
| | 30 | 92 | | |
| 2 | 100 | 67 | 30 | −56 |
| | 30 | 83 | 10 | −20 |
| 3 | 100 | 83 | 30 | −77 |

-continued

Pharmacological Test Results

| Compound [Product of Example No.] | Stress-induced erosion (Senay & Levine) | | Anti-secretory (Shay et al) | |
|---|---|---|---|---|
| | Dose mg/kg | % inhibition | Dose mg/kg | % change in Vol. |
| 4 | 100 | 67 | 30 | −45 |
| 5 | 100 | 70 | 30 | −65 |
| | | | 10 | −35 |
| 6 | 100 | 84 | 30 | NS |
| 7 | 100 | 77 | 30 | NS |
| 8 | 100 | 62 | 30 | NS |
| | 30 | 70 | | |
| 9 | 100 | — | 30 | −32 |
| 10 | 100 | — | 30 | −43 |
| 11 | 100 | 62 | 30 | −70 |
| | | | 10 | −42 |
| 12 | 100 | 87 | 30 | NS |
| | 30 | 67 | | |
| | 10 | 64 | | |
| 13 | 100 | 70 | 30 | NS |
| | 30 | 73 | | |
| 14 | 100 | 90 | 30 | −49 |
| | 30 | 73 | 10 | −19 |
| | 10 | 60 | | |
| 15 | 100 | 100 | 30 | NS |
| 16 | 100 | — | 30 | −55 |
| 17 | 100 | 64 | 30 | −52 |
| 18 | 100 | 71 | 30 | −39 |
| | 30 | 60 | | |
| 19 | 100 | — | 30 | −88 |
| 20 | 100 | 70 | 30 | −90 |
| | 30 | 76 | 10 | −54 |
| 21 | 100 | 82 | 30 | −67 |
| | 30 | 71 | | |
| 22 | 100 | 72 | 30 | −69 |
| | 30 | 64 | | |
| 23 | 100 | 80 | 30 | NS |
| | 30 | 70 | | |
| 24 | 100 | 23 | 30 | −40 |
| | 30 | 60 | | |
| 25 | 100 | 80 | 30 | −69 |
| | 30 | 75 | | |
| 26 | 100 | — | 30 | −46 |
| 27 | 100 | — | 30 | −66 |
| | | | 10 | −39 |
| 28 | 100 | — | 30 | −55 |
| 29 | 100 | 71 | 30 | −48 |
| 30 | 100 | 71 | 30 | −42 |
| 31 | 100 | 62 | 30 | −34 |
| 32 | 100 | 73 | 30 | NS |
| 33 | 100 | 73 | 30 | NS |
| 34 | 100 | 64 | 30 | NS |
| 35 | 100 | 67 | 30 | −41 |
| 36 | 100 | 69 | 30 | NS |
| 37 | 100 | — | 30 | NS |
| 38 | 100 | — | 30 | −32 |
| 39 | 100 | — | 30 | NS |
| 40 | 100 | 67 | 30 | −36 |
| 41 | 100 | 69 | 30 | NS |
| 43 | 100 | — | 30 | −48 |
| 44 | 100 | — | 30 | −52 |
| 45 | 100 | — | 30 | −75 |

NS = Not Significant

ANTIHYPERTENSIVE ACTIVITY

Some compounds of the invention were tested for antihypertensive activity by the following procedures

Procedure A

Systolic pressure of male spontaneously hypertensive rats is measured by an indirect technique using the Decker Caudal Plethysmograph or other appropriate sensor. Groups usually consist of 4 rats. Drugs are usually administered orally. Pressures are usually read prior to drug administration and at 1.5, 4 and 24 hours thereafter. This schedule may be altered depending upon the behaviour of the drug.

Compounds of the following examples showed activity in this test at the dose stated. 75 mg/kg orally: Examples 2, 4, 5 and 15, 50 mg/kg orally:Example 37 and 39.

Compounds of the following examples were inactive in this test at the oral dose stated. Examples 3, (75 mg/kg), 17 and 18 (50 mg/kg).

Procedure B

Female rats are rendered hypertensive by unilateral nephrectomy and the s.c. implantation of a pellet containing 30 mg of deoxycorticosterone acetate. The drinking water is replaced by normal saline ad lib for the first four weeks following preparation. Blood pressures stabilise at a hypertensive level after 6 weeks. Systolic pressure is measured indirectly before dosing with a test compound using an E and M pneumatic pulse transducer and a Devices MX2 recorder. Groups of 4 rats are dosed orally with suspensions or solutions of the test compound in 0.5% hydroxypropyl-methylcellulose 0.9% saline vehicle. Blood pressures are recorded again at 2, 6 and 24 hours and the results, expressed as a percentage of the pre-dose values compared with those of a similar group of rats receiving vehicle alone.

The compounds of Example 11 and 12 were inactive in this test at 50 mg/kg orally.

PHARMACEUTICAL COMPOSITIONS

The following examples illustrate the preparation of unit dosage form of pharmaceutical compositions according to the invention.

EXAMPLE A

| AntacidTablet (chewable) | |
|---|---|
| Saccharin | 1.0 mg. |
| Hydrated alumina sucrose powder | 750.0 mg. |
| 2-Benzylthio-1-methylpyridinium bromide | 100.0 mg. |
| Mannitol B.P. | 170.0 mg. |
| Maize starch B.P. dried | 30.0 mg. |
| Talc. purified B.P. | 28.0 mg. |
| Magnesium stearateB.P. | 20.0 mg. |
| Peppermint oil B.P. | 1.0 mg. |
| | 1100.0 mg. |

Antacid tablets of the above formulation are prepared by the following procedure. Triturate peppermint oil with talc (screen 40 mesh). Add the triturate, and other ingredients to a blender and mix thoroughly. Slug the powder to large hard slugs. Granulate the slugs through a 14 mesh screen. Compress the granules on a suitable compression machine to give tablets of the required size.

EXAMPLE B

| Anti-ulcer tablet (without antacid) | mg/tablet |
|---|---|
| 2-Benzylthio-1-methylpyridinium bromide | 100 mg. |
| Celutab | 147.5 mg. |
| Mg. Stearate | 2.5 mg. |
| | 250.0 mg. |

The tablets are prepared by the following method. Blend the ingredients in a suitable blender. Compress the blended ingredients on a suitable compression machine to form tablets of the above composition. Celutab is a commercial product comprising 90-2% dextose, 3-5% maltose, the remainder being higher glucose saccharides. The product is spray crystallised.

EXAMPLES C to R

Examples A is repeated but replacing 2-benzylthio-1-methyl-pyridinium bromide with 100 mg of the products of Examples 2, 3, 5, 11, 14, 16, 17, 19, 20, 21, 22, 25, 26, 27, 28 and 30 respectively.

Examples I to XVI

Example B is repeated but replacing 2-benzylthio-1-methyl-pyridinium bromide with 100 mg of the products of Examples 2, 3, 5, 11, 14, 16, 17, 19, 20, 21, 22, 25, 26, 27, 28, 30, 31, 35, 38, 40, 43, 44 and 45 respectively.

I claim:

1. A method for treating ulcers or hypersecretion in a mammal which comprises administering to said mammal an effective amount of a compound of formula I

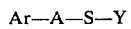   I wherein Ar represents a cycloalkyl group of 5 to 7 carbon atoms, or a phenyl group which may be substituted by one or more of the following: halogen, nitro, lower alkoxy, hydroxy, hydroxyloweralkyl, loweralkoxyloweralkyl, amino, loweralkylamino, aralkoxy, diloweralkylamino, loweralkyl, aryl or aralkyl of 7 to 10 carbon atoms or disubstituted by a loweralkylenedioxy radical; A represents a saturated or olefinically unsaturated alkylene radical having from 1 to 6 carbon atoms, which may be substituted by lower alkyl of 1 to 6 carbon atoms, oxo, or hydroxy, S is sulphur and Y is a radical of formula

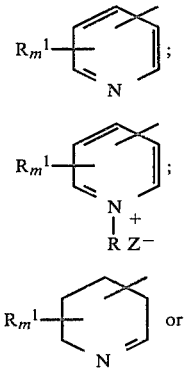

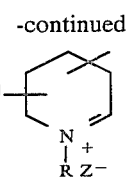

wherein $R^1$ is hydrogen, lower alkyl, hydroxylower alkyl, loweralkoxyloweralkyl, loweralkoxy, halogen, formyl, phenyl, phenylalkyl or acetal i.e. $CH(OR^4)_2$ where $R^4$ is lower alkyl or two $R^4$ radicals are joined to form a lower alkylene chain, R is lower alkyl of 1-4 carbon atoms, aryl or aralkyl of 7 to 12 carbon atoms, m is 1 or 2 and $Z^-$ is an anion, or an acid addition salt of a compound containing a radical of formula II or IIa, with the proviso that when Y is a radical of formula II, Ar is other than aralkoxyphenyl.

2. A method as claimed in claim 1, wherein the compound of formula I is one in which A is $-CH_2-$.

3. A method as claimed in claim 1, wherein the compound of formula I is one in which Ar is mono- or dihalophenyl.

4. A method as claimed in claim 1, wherein the compound of formula I is a compound of formula

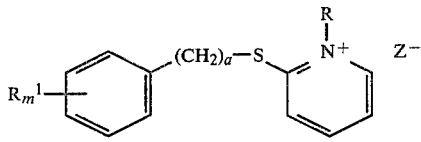

wherein R is lower alkyl of 1-4 carbon atoms or benzyl, $R^1$ is halogen, $Z^-$ is a halide ion, n is 1 or 2 and a is 1 or 2.

5. A method as claimed in claim 1, wherein the compound of formula I is 1-methyl-2-(2-phenylethylthio)-pyridinium bromide.

6. A method as claimed in claim 1, wherein the compound of formula I is 2-(2,6-dichlorobenzylthio)-1-methylpyridinium chloride.

7. A method as claimed in claim 1, wherein the compound of formula I is 1-methyl-2-(3-chlorobenzylthio)-pyridinium chloride.

8. A method as claimed in claim 1, wherein the compound of formula I is 2-(((-4-benzyloxy)benzyl)thio)-1-methylpyridinium chloride.

9. A method as claimed in claim 1, wherein the compound of formula I is 2-((2-fluorobenzyl)thio)-1-methyl-pyridinium chloride.

10. A method as claimed in claim 1, wherein the compound of formula I is 2-((2-chlorobenzyl)thio)-1-methylpyridinium chloride.

11. A solid anti-ulcer composition for oral administration to a mammal, consisting essentially of a mixture of 10 to 500 mg. of a compound of formula I as defined in claim 1, and a pharmaceutically acceptable solid carrier, in oral unit dosage form.

* * * * *